United States Patent [19]

Izumi

[11] 4,281,288

[45] Jul. 28, 1981

[54] APPARATUS FOR THE MEASUREMENT OF THE MECHANICAL OUTPUT OF INDUCTION MOTORS

[75] Inventor: Kaichi Izumi, Tokyo, Japan

[73] Assignee: Kao Soap Company Limited, Tokyo, Japan

[21] Appl. No.: 59,261

[22] Filed: Jul. 20, 1979

[30] Foreign Application Priority Data

Jul. 21, 1978 [JP]  Japan ................................. 53-89162
Nov. 30, 1978 [JP]  Japan ................................ 53-148182

[51] Int. Cl.³ .................... G01R 31/00; G01N 11/02; G01R 1/38
[52] U.S. Cl. .............................. 324/158 MG; 73/54; 324/74; 324/110; 324/161
[58] Field of Search ............... 324/158 MG, 161, 166, 324/115, 110, 74; 73/54, 59

[56] References Cited

U.S. PATENT DOCUMENTS 3,758,858  9/1973  McCue ................................. 324/115
4,184,114  1/1980  Minakuchi .......................... 324/161

OTHER PUBLICATIONS

Hellar, Jr., "Precision Speed . . . ", General Electric Review, Oct. 1949, pp. 22-26.

Primary Examiner—Ernest F. Karlsen
Attorney, Agent, or Firm—Philip M. Hinderstein

[57] ABSTRACT

Apparatus for measuring and/or supervising the output power of an induction motor comprising means for generating a first voltage signal proportional to the synchronous speed of the motor, means for generating a second voltage signal proportional to the actual speed of the motor in operation and means responsive to the first and second voltage signals for generating a third voltage signal proportional to the difference between the first and second voltage signals. The third voltage signal is applied to a meter for providing a continuous indication of the output power of the motor.

9 Claims, 6 Drawing Figures

APPARATUS FOR THE MEASUREMENT OF THE MECHANICAL OUTPUT OF INDUCTION MOTORS

BACKGROUND OF THE INVENTION

1. Field of the Invention

The present invention relates to apparatus for the measurement of the mechanical output of induction motors and, more particularly, to circuit means for providing a quick and easy measurement of the output power of an induction motor.

2. Description of the Prior Art

It is widely known that the mechanical output of rotary machines is given by the product of torque and rotary speed. Both torque and rotary speed are measurable by commercially available instruments. However, before one can measure torque using available instruments, the installation of a load cell is usually required and the capacity and sensitivity of such load cell must be decided upon depending upon the object of the measurements. The labor required to install the load cell is undesirable when one wants quick and easy measurements and the selection of a load cell limits the versatility of the measuring instrument.

It is also known that a watt-hour meter is capable of measuring the electric power consumption of an induction motor independently of the power factor. This being the case, the difference of the readings obtained for a motor operating with and without a load corresponds to the mechanical output of the motor. However, with this type of measurement, the selection of the watt-hour meter depending upon the consumption of the motor and wiring of the meter to the motor are required. These requirements are similarly undesirable as was the case with the requirements of torque measurements. In addition, a watt-hour meter does not indicate the instantaneous consumption of electric power. Rather, it only indicates accumulative consumption. This is undesirable when the measurement is done to trace varying load conditions of the motor.

By using three ammeters, one can obtain an instantaneous reading of power consumption. However, it is virtually impossible for the average person to read three ammeters at a time, especially when loading conditions are quickly changing.

For most induction motors manufactured and sold commercially, the relationship between torque and current and/or torque and rotary speed are known. By using a tachometer or an ammeter, the output of the motor is measurable, although calculations based upon the above-mentioned relationship are required. Between measurements made by an ammeter and by a tachometer, the latter is preferred because no wiring and no selection of capacity are required.

Among the known measuring methods mentioned hereinabove, the method which employs a tachometer seems to be the best as far as simplicity is concerned, but a serious problem still exists, as will now appear. Specifically, FIG. 1 shows the relationship between mechanical output (torque) and the rotary speed of a typical induction motor, where Tm is rated maximum output, H is the rotary speed at rated maximum output, and S is synchronous speed. Synchronous speed (S) is calculated from the line frequency (f) and the number of poles of the motor (P) by the following equation, which is independent of the output capacity:

$$S = 120 f/P. \tag{1}$$

The slip of an induction motor is proportional to the difference between the synchronous speed and the actual speed as follows:

$$Sl = (S-H)/S \times 100\%, \tag{2}$$

where Sl is the slip.

For most induction motors, slip as rated maximum ranges from 0.3 to 5%. Due to the very small value of slip, only a very narrow portion of the scale of a tachometer is useful as an effective reading range and precision of the scale reading is very poor. For example, if one is to determine the output of a 4-pole motor, the slip of which is 5% and which is operated at a line frequency of 50 Hz, the rotary speed of the motor varies from 1500 to 1425 rmp as the load changes from 0-100% of the rated maximum. Assuming that the tachometer has a scale of 0 to 1500 rmp divided by 100, misreading of one division causes only a 1% error when it is used as a tachometer but when the tachometer is used as an output meter, the same misreading causes a 20% error.

The direct use of a tachometer as an output meter has another disadvantage. That is, the higher the output of the motor, the lower the indication on the scale. Such an output indication is against human nature.

SUMMARY OF THE INVENTION

According to the present invention, there is provided apparatus for the measurement of the mechanical output of induction motors which solves these problems in a manner unknown heretofore. With the present invention, quick and easy measurements are permitted without the requirement of mechanical labor to install a load cell. The present apparatus also provides an indication of instantaneous mechanical output. The present apparatus is versatile and not subject to significant error. Furthermore, as the output of the motor increases, the output indication increases proportionately.

Briefly, the present apparatus for the measurement for the mechanical output of induction motors comprises means for generating a first voltage signal proportional to the synchronous speed of the motor, means for generating a second voltage signal proportional to the actual speed of the motor in operation and means responsive to the first and second voltage signals for generating a third voltage signal proportional to the difference between the first and second voltage signals. The third voltage signal is applied to a meter for providing a continuous indication of the output power of the motor. Auxiliary circuits are also provided for additional performance such as alarming and/or controlling and for better convenience of making measurements.

OBJECTS, FEATURES AND ADVANTAGES

It is therefore an object of the present invention to solve the problems associated with existing apparatus for the measurement of the mechanical output of induction motors. It is a feature of the present invention to solve these problems by providing circuit means which calculates the difference between the synchronous speed of a motor and the actual speed of the motor. An advantage to be derived is that the mechanical output of an induction motor can be determined quickly and easily. A further advantage is that instantaneous output can be provided. A still further advantage is that the present apparatus is versatile. Another advantage is that the present apparatus is not subject to significant error.

Still other objects, features, and attendant advantages of the present invention will become apparent to those skilled in the art from a reading of the following detailed description of the preferred embodiment constructed in accordance therewith, taken in conjunction with the accompanying drawings wherein:

DESCRIPTION OF THE PREFERRED EMBODIMENT

Figure 1:
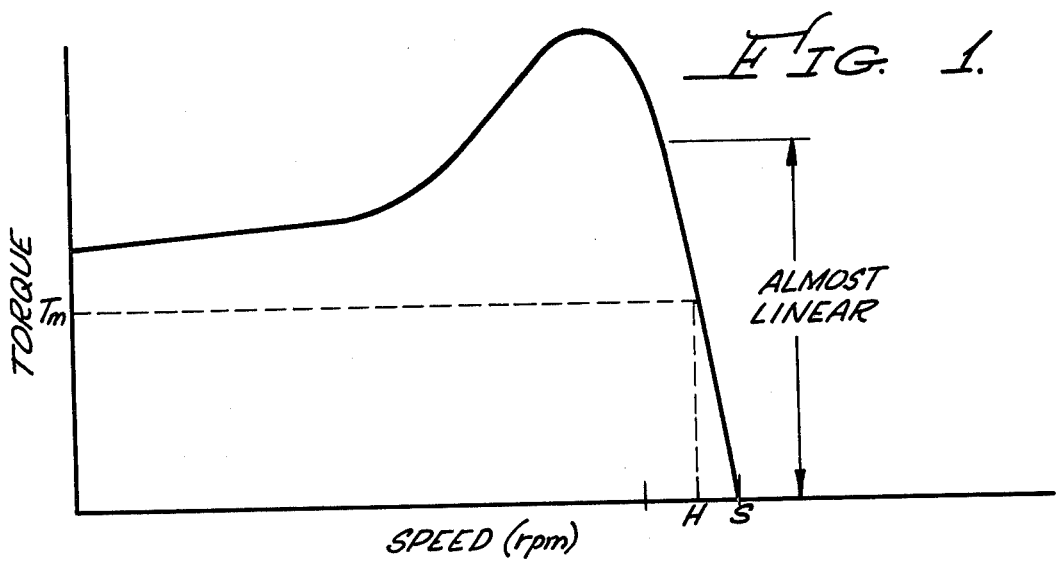
FIG. 1 is a curve showing the relationship between mechanical output and rotary speed of an induction motor.

As shown in FIG. 1, almost all induction motors have an almost linear section on the curve of torque versus speed and this linear section is at the speeds near the synchronous speed where an induction motor commonly operates. Advantage of this is taken with the present invention.

Figure 2:
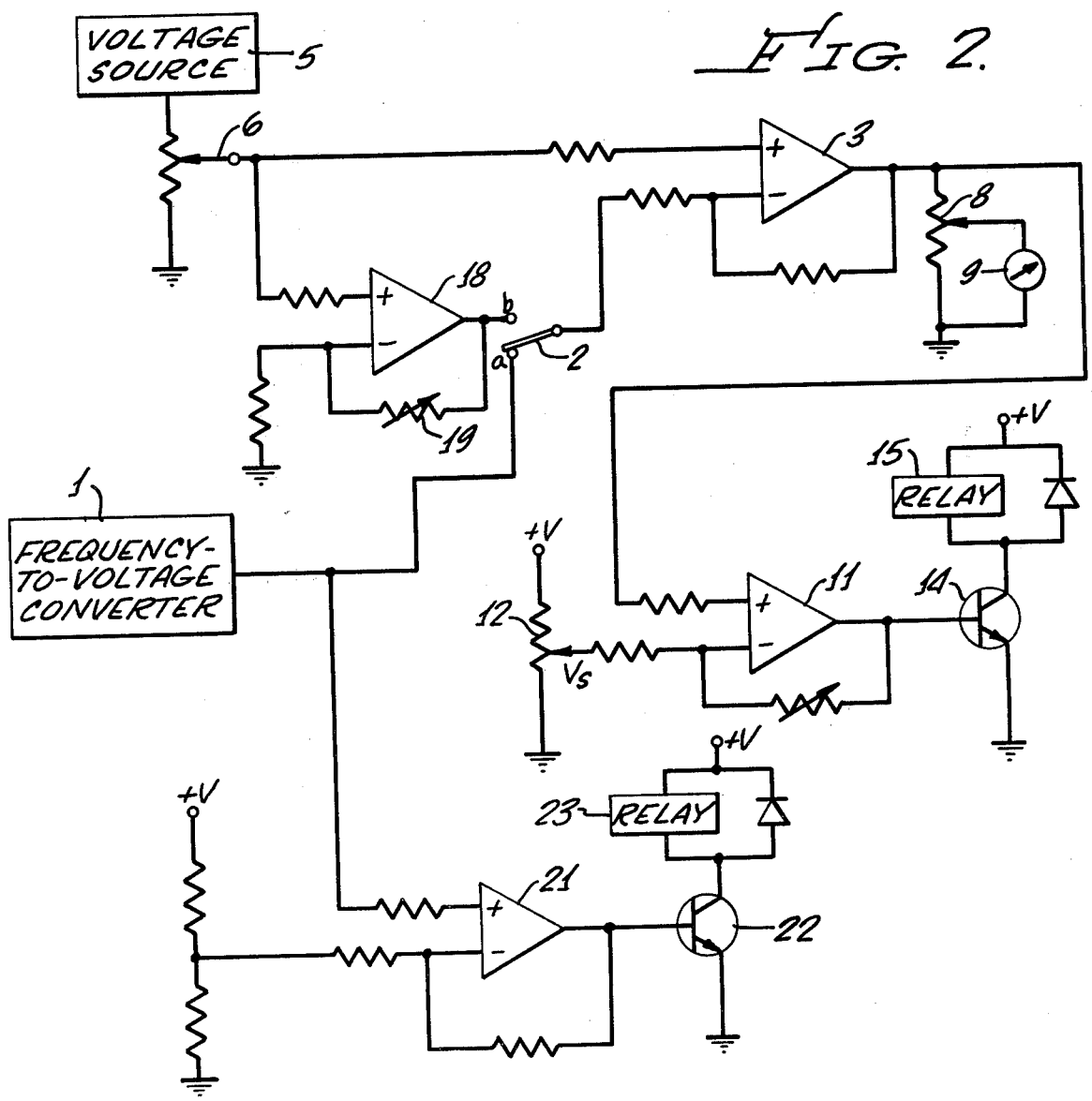
FIG. 2 is a fundamental circuit diagram of the present invention.

Referring now to FIG. 2, voltage source 5 is a source of a voltage signal corresponding to the frequency of the electric source for an induction motor. Voltage source 5 may either be a rectified and stabilized DC voltage or the output of a frequency-to-voltage converter taking the frequency of the electric source as its input signal. The latter is theoretically better than the former because the output automatically follows the change of the synchronous speed, but the former is more practical and simpler if the frequency is stable enough, which is usually the case. In any event, because of the proportionality of synchronous speed to the source frequency, the voltage signal from source 5 corresponds to synchronous speed (S). The output of voltage source 5 is connected to a potentiometer 6 which may be utilized to adjust the voltage as needed.

The output of potentiometer 6 is connected to the noninverting inputs of two operational amplifiers 3 and 18. The signal applied to amplifier 18 is either amplified or reduced in value by the adjustment of a variable resistor 19 connected between the output and the inverting input thereof in order to provide a voltage (H) at the output of operational amplifier 18 which differs from the input voltage thereto by an amount corresponding to the known slip (Sl) of the motor. This is calculated from equation (1). With switch 2 held at position "b", this voltage signal is applied to the inverting input of amplifier 3 so that the output of amplifier 3 now corresponds to the synchronous speed (S) less H, the rotary speed at rated maximum output. The output of amplifier 3 is conducted to a meter 9 via an adjustble potentiometer 8 which can now be adjusted so that meter 9 is made full scale.

A frequency-to-voltage converter 1 generates a voltage signal (Ha) proportional to the rotary speed of the motor in operation. With the adjustments described above and with switch 2 in position "a", meter 9 will indicate 0 to 100% when the output of the induction motor varies from 0 to Tm following a change in speed from S to H.

The output of frequency-to-voltage converter 1 is also applied to an operational amplifier 21, the output of which is coupled to a transistor 22, amplifier 21 and transistor 22 forming a driving circuit for a relay 23 which holds switch 2 at position "b" when the output voltage from converter 1 is lower than that corresponding to H to protect meter 9 from an over scale reading.

The output of amplifier 3 is applied to a non-inverting input of an operational amplifier 11, the inverting input of which is connected to a potentiometer 12 which establishes a control limit voltage Vs. The output of amplifier 11 is connected to a transistor 14, amplifier 11 and transistor 14 driving a relay 15 for the control of outside equipment.

Frequency-to-voltage converter 1 may either be a small generator, the output voltage of which is proportional to the rotary speed of the motor, or a frequency-to-voltage converter which takes the AC current from an electro-magnet or photo-electric sensor and converts it into a DC voltage signal proportional to the input frequency. The converting circuit may either be assembled using discrete devices or be an integrated circuit which functions as a digital-to-analog converter.

Operational amplifier 3 functions as a differential amplifier and may either be an integrated circuit or be assembled from discrete components.

Amplifier 18 may be replaced by a dividing circuit consisting of two fixed resistors or it may be entirely eliminated if the apparatus is used constantly to determine the output of a single motor. Under such circumstances, the source frequency, the synchronous speed, and slip are constant. Under such circumstances, full scale adjustment can be done during assembly of the apparatus. Therefore, potentiometer 8 could be a semi-fixed resistor.

The apparatus of FIG. 2 may be operated from a commercial AC line or by suitable batteries. In either case, the supply voltage to the various devices is preferably stabilized or, at least, the voltage to source 5 should be stabilized if the voltage signal for a synchronous speed is given by a dividing circuit, as shown.

Figure 3:
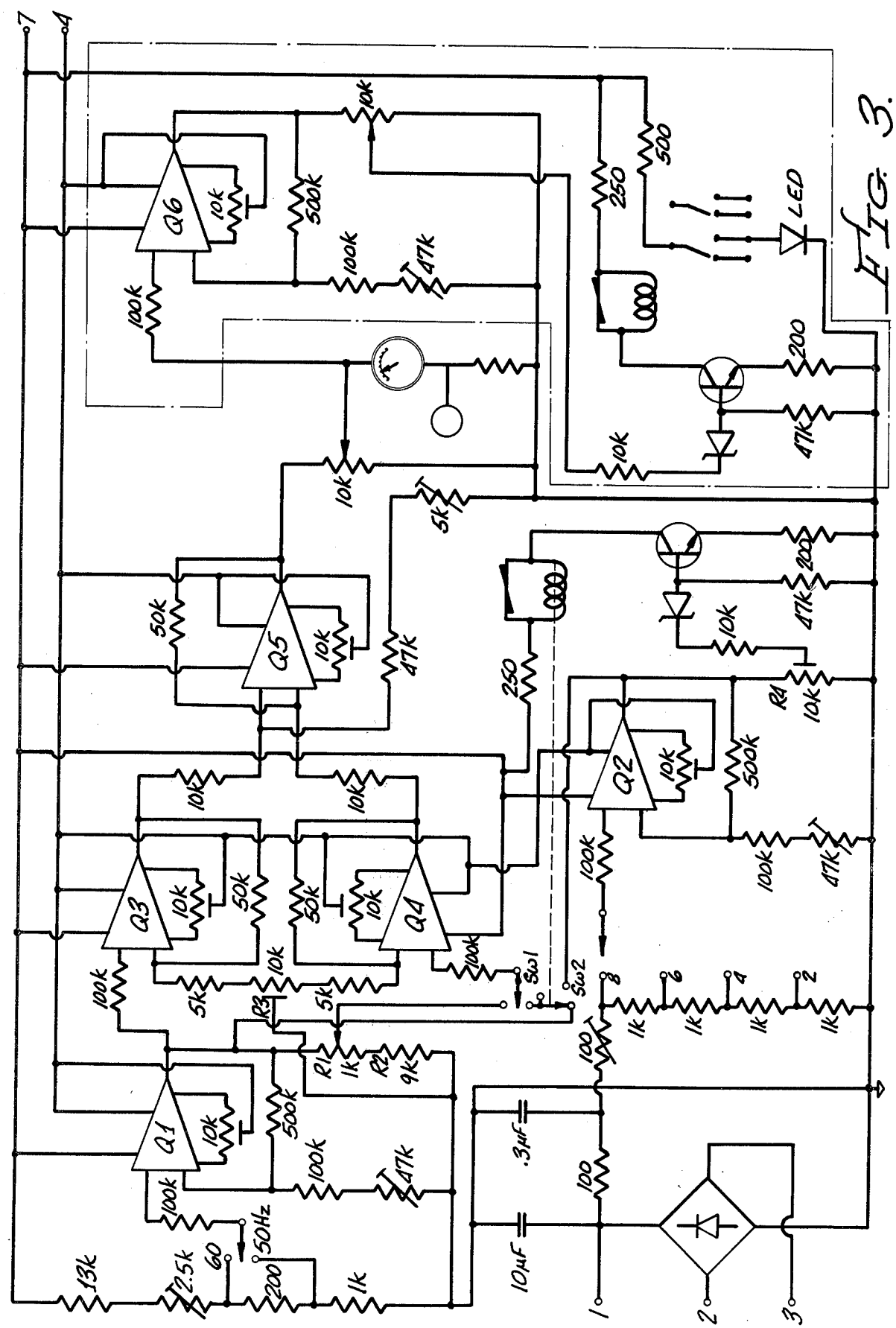
FIG. 3 is an example of an actual circuit diagram of the present invention.

Turning now to FIG. 3, there is shown an example of an actual circuit diagram of the present invention. Obviously, the present invention is not limited to the apparatus shown in FIG. 3. All components except by-pass condensors, (0.1 uf) connected between pins 4 and 7 of each operational amplifier Q1–Q6 and ground and a DC power source are shown in FIG. 3. The circuit component surrounded by the broken line is for the control of outside equipment and may be omitted or replaced by a meter-relay. The diode bridge at terminals "2" and "3" may be omitted if a DC tachometer/generator or a digital-to-analog converter is used as a sensor for rotary speed.

In relation to the circuit of FIG. 2, operational amplifiers Q3, Q4, and Q5 form a differential amplifier which is equivalent to operational amplifier 3 and operational amplifier Q1 is equivalent to operational amplifier 18. Operational amplifier Q2 is used as a buffer amplifier for a differential input and as an amplifier for over-scale protection which is equivalent to operational amplifier 21 in FIG. 2.

In the operation of the circuit of FIG. 3, the switch at the non-inverting input of amplifier Q1 is for the selection of the frequency of the AC line. The switch at the input of amplifier Q2 is for the selection of the number of poles of the induction motor. With the motor, the mechanical output of which is to be measured, running at synchronous speed, the output voltages of both amplifiers Q1 and Q2 have to be equal. The two variable resistors at the inverting inputs of these amplifiers are for adjustment of the amplitudes thereof to make the two output voltages equal. The output of amplifier Q1 is divided by variable resistor R1 and fixed resistor R2. The ratio of $R_1/(R_1+R_2)$ determines the maximum allowable slip (from equation 1) of the apparatus. The shaft of resistor R1 is connected mechanically to a precision dial to allow the setting of the slip, depending upon the motor to be measured.

If the input of amplifier Q4 is constantly connected to the output of amplifier Q2, the differential input voltage would exceed the allowable limit to make the meter read full scale until the speed of the motor reaches H in FIG. 1. To prevent this, before the measurement, switch Sw1 is held at an adjust position in which the input of amplifier Q4 is connected to R1, R1 being set at the slip of the motor, and the output resistor of amplifier Q5 is adjusted to make the meter read full scale. To protect the meter from an over-scale condition, the measure position of switch Sw1 is connected to the transfer contact of a switch Sw2 and the input of amplifier Q4 is connected to the output of amplifier Q1 through switches Sw1 and Sw2 making the differential input voltage 0. Thus, at the position of switches Sw1 and Sw2 shown in FIG. 3, zero calibration of the meter may be done by adjusting resistor R3 between the two inverting inputs of amplifiers Q3 and Q4. Resistors R1 and R4 may be fixed resistors for a fixed installation on a particular equipment. By using two variable resistors on one shaft in place of resistors R1 and R4, the setting of the switching position of switch Sw2 is made much easier, although changes in the resistors and zener diode are required. The resistor between the meter and ground provides an output terminal to be used for a chart recorder or other outside indicator.

After the adjustments of full scale and zero and with switch Sw1 at the "measure" position, the apparatus is ready for making measurements. The meter will indicate mechanical output of a motor in terms of percentage of full load (Tm).

In the construction field, the flowability of concrete before hardening is very important for the efficiency and for the compactability of placement. Flowability is usually exhibited by slump which is a loss in height of concrete filled in a slump cone after removal of the cone. As is well known, concrete starts losing its flowability shortly after the addition of water. To maintain the flowability for some time before placement, a flowing aid or a water reducing admixture is frequently used and to use such chemicals properly, automatic or continuous measurement of the flowability is desirable.

Figure 4:
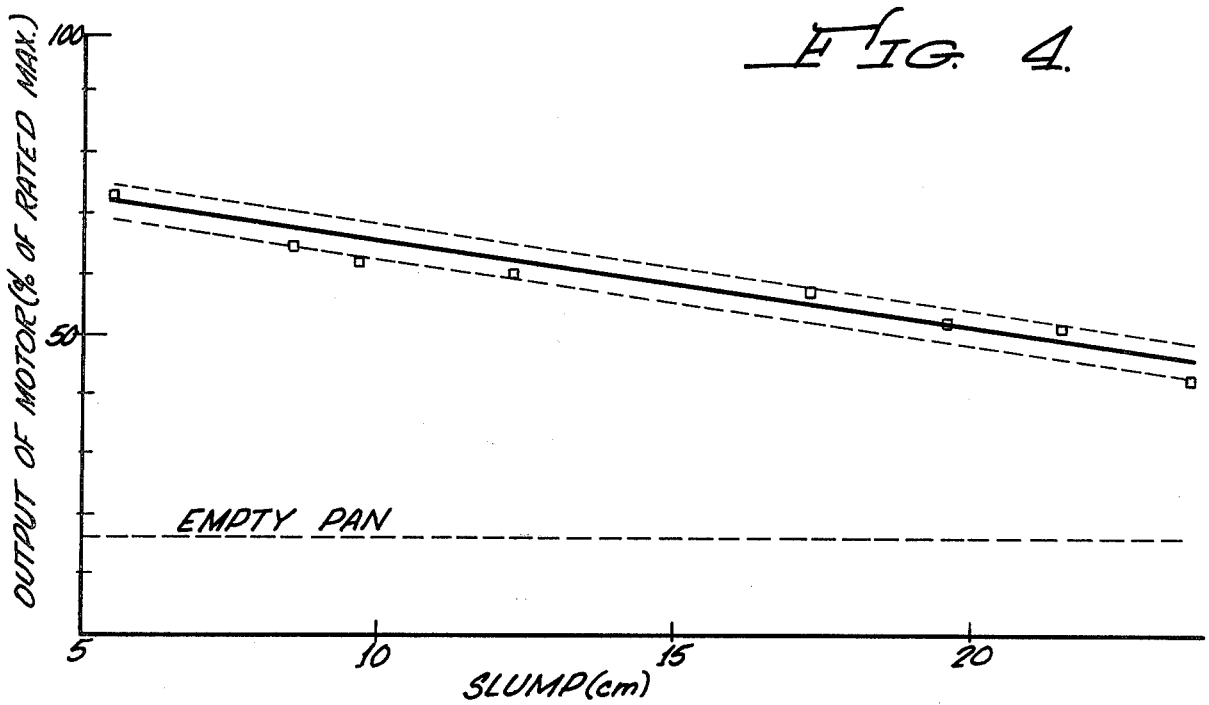
FIGS. 4 and 5 show curves obtained with the apparatus of FIG. 3 when using an induction motor to determine the flowability of concrete.
Figure 5:
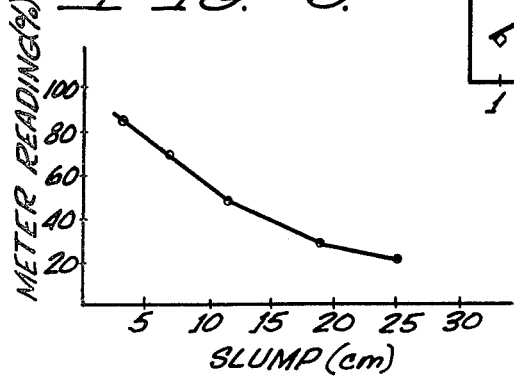

FIGS. 4 and 5 show the relationship between the flowability of concrete and the mechanical output of motors which drive forced stirring pan mixers, these curves being obtained by the apparatus of FIG. 3. FIG. 4 shows the output of the motor as a percent of rated maximum as a function of slump. FIG. 5 shows the actual meter reading as a function of slump. Both of these curves were actually obtained by the apparatus of FIG. 3. As a further experiment, the slump of concrete in a mixer was maintained at 15±3 cm for more than two hours by controlling the admixture pump using the apparatus of FIG. 3.

Figure 6:
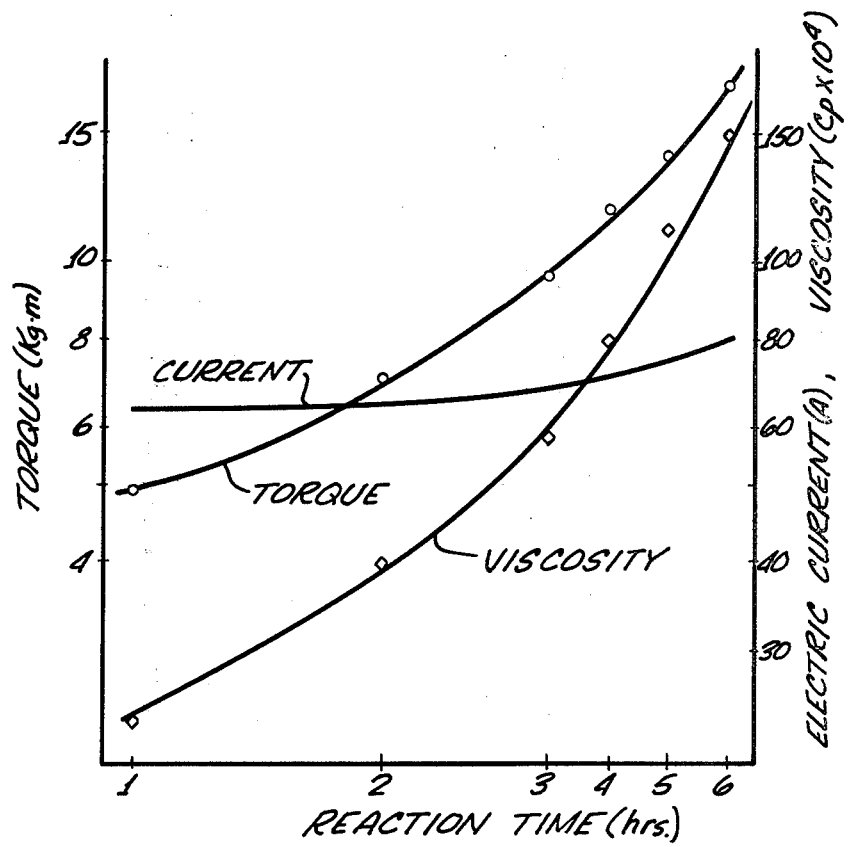
FIG. 6 is a series of curves further showing the usefulness of the present apparatus for an induction motor installed to agitate a reaction mixture in the vessel of a chemical reaction.

The curve of FIG. 6 shows another example of the usefulness of the apparatus of the present invention. The graph of FIG. 6 which shows torque, viscosity, and electric current versus reaction time was obtained for an induction motor installed to agitate the reaction mixture in the vessel of a chemical reaction. In the vessel, as the reaction progresses, viscosity of the mixture increases. This type of reaction is very popular in the chemical industry in the synthesis of polymeric substances. To have the product of proper quality, the reaction has to be stopped at a viscosity of approximately 1,500,000 centi poise. If the reaction is not stopped at the proper time, the product becomes too viscous to be removed from the vessel or the entire content solidifies damaging the agitator and the whole reaction system.

As shown in FIG. 6, the change in the reading of ammeter is very narrow. Therefore, reliable control of the reaction is not expected if an ammeter is used for the detection of viscosity. On the other hand, the output torque of a motor detected by the apparatus of the present invention is much better in controlling the reaction because of higher sensitivity and traceability than the reading of an ammeter.

Part of the uniqueness of the present apparatus is the very wide coverage of measuring range. The present apparatus can measure the output of an induction motor operated either by a single phase or a three phase AC line or operated by varieties of line frequency. The present apparatus is capable of measuring the output of a motor independently from the line voltage in which the motor is operated. The output capacity of the motor does not restrict usage of the present apparatus except when the output is very small. To generate a voltage signal corresponding to the actual rotary speed, the present apparatus consumes a very low torque equivalent to less than a few watt-hours. This may cause some error in the measurement if the output of the motor is less than a few watt-hours maximum.

I claim:

1. An apparatus for measuring and/or supervising the output of an induction motor comprising:

means for generating a first voltage signal (S) corresponding to the synchronous speed of said motor;

means for generating a second voltage signal (H) proportional to the rotary speed of said motor at rated maximum output;

means for generating a third voltage signal (Ha) proportional to the rotary speed of said motor in operation;

circuit means responsive to said first voltage signal and either said second or third voltage signals for generating voltage signals proportional to S-H or S-Ha;

means for switching the second voltage signal or the third voltage signal to said circuit means;

indicator means responsive to the output of said circuit means; and means operative when the first voltage signal and the second voltage signal are applied to said circuit means for adjusting the full scale indication of said indicator means, said switching means thereafter enabling the application of the third voltage signal to said circuit means so that said indicator means indicates S-Ha.

2. An apparatus according to claim 1, wherein said circuit means comprises:
a differential amplifier.

3. An apparatus according to claim 2, further comprising:
means responsive to said third voltage signal for generating an over-scale signal for the protection of said indicator means.

4. An apparatus according to claim 3, wherein said switching means comprises:
an automatic switching circuit responsive to said third voltage signal for switching the input of said differential amplifier between said second and third voltage signals.

5. An apparatus according to claim 1, further comprising:
circuit means responsive to said signal proportional to S-Ha for transmitting a signal for the control of other equipment associated with said motor.

6. An apparatus according to claim 1, further comprising:
an output terminal responsive to said signal proportional to S-Ha for connection to an external indicator.

7. An apparatus according to claim 1, further comprising:
a digital meter responsive to said circuit means.

8. An apparatus according to claim 1, wherein said third voltage signal generating means comprises:
an AC generator.

9. An apparatus according to claim 1, wherein said third voltage signal generating means comprises:
a DC generator.

* * * * *